US006585767B1

(12) United States Patent
Holley et al.

(10) Patent No.: US 6,585,767 B1
(45) Date of Patent: **\*Jul. 1, 2003**

(54) ANTIMICROBIAL SUTURING RING FOR HEART VALVE

(75) Inventors: Steven Holley, Brighton, MA (US); John E. Barry, Derry, NH (US); Jeffrey A. Trogolo, Boston, MA (US)

(73) Assignee: AgION Technologies, Inc., Wakefield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/197,808

(22) Filed: Nov. 23, 1998

(51) Int. Cl.[7] .................................................. A61F 2/24
(52) U.S. Cl. ...................... 623/2.41; 623/2.42; 623/926
(58) Field of Search .............................. 623/2.41, 2.42, 623/2.1, 924, 926

(56) References Cited

U.S. PATENT DOCUMENTS

| | | | |
|---|---|---|---|
| 4,775,585 A | 10/1988 | Hagiwara et al. | 428/323 |
| 4,906,464 A | 3/1990 | Yamamoto et al. | 424/78 |
| 4,911,898 A | 3/1990 | Hagiwara et al. | 423/118 |
| 4,911,899 A | 3/1990 | Hagiwara et al. | 423/118 |
| 4,923,450 A | 5/1990 | Maeda et al. | 604/265 |
| 4,938,955 A | 7/1990 | Niira et al. | 424/79 |
| 4,938,958 A | 7/1990 | Niira et al. | 424/79 |
| 5,009,898 A | 4/1991 | Sakuma et al. | 424/618 |
| 5,019,096 A | 5/1991 | Fox, Jr. et al. | 623/1 |
| 5,100,671 A | 3/1992 | Maeda et al. | 424/443 |
| 5,102,401 A | 4/1992 | Lambert et al. | 604/264 |
| 5,157,005 A | 10/1992 | Suppiah | 502/62 |
| 5,180,585 A | 1/1993 | Jacobson et al. | 424/405 |
| 5,244,667 A | 9/1993 | Hagiwara et al. | 424/409 |
| 5,296,238 A | 3/1994 | Sugiura et al. | 424/604 |
| 5,305,827 A | 4/1994 | Steele et al. | 165/133 |
| 5,405,644 A | 4/1995 | Ohsumi et al. | 427/2.31 |
| 5,441,717 A | 8/1995 | Ohsumi et al. | 423/306 |
| 5,474,797 A | 12/1995 | Sioshansi et al. | 427/2.24 |
| 5,492,763 A | 2/1996 | Barry et al. | 428/457 |
| 5,509,899 A | 4/1996 | Fan et al. | 604/96 |

(List continued on next page.)

FOREIGN PATENT DOCUMENTS

| | | |
|---|---|---|
| WO | WO 96/30060 | 10/1996 |
| WO | WO 98/14139 | 4/1998 |

OTHER PUBLICATIONS

Sax et al, Hawley's Condensed Chemical Dictionary, (1987), Van Nostrand Reinhold Company, 11 ed., p. 1016.*

Primary Examiner—Paul B. Prebilic
(74) Attorney, Agent, or Firm—Edward K. Welch, II

(57) ABSTRACT

A suturing ring to attach the body of an implantable heart valve to heart tissue by sutures is composed of a fabric containing an inorganic antimicrobial agent. The fabric can have a material coating the fibers of the fabric in which particles of the agent are embedded. The coating material can be elastomeric and the fabric porous, to improve its flexibility, or non-porous and the fabric ring can be coated with a tissue compatible substance such as collagen. One type of ring has an annular top part to fit over one of top and bottom surfaces of the valve body and defining an opening to the heart valve, a step wall depending from the annular top part to extend along said valve body wall and an outwardly extending flange through which the sutures are to be sewn.

24 Claims, 2 Drawing Sheets

U.S. PATENT DOCUMENTS

| | | |
|---|---|---|
| 5,520,664 A | 5/1996 | Bricault, Jr. et al. ......... 604/265 |
| 5,556,699 A | 9/1996 | Niira et al. .................. 428/323 |
| 5,562,872 A | 10/1996 | Watanabe ................... 264/145 |
| 5,607,464 A | 3/1997 | Trescony et al. .............. 623/1 |
| 5,674,280 A | 10/1997 | Davidson et al. .............. 623/2 |
| 5,697,203 A | 12/1997 | Niwa .......................... 53/510 |
| 5,714,430 A | 2/1998 | Gehrer et al. ................ 502/347 |
| 5,714,445 A | 2/1998 | Trinh et al. ................. 510/103 |
| 5,723,110 A | 3/1998 | Yamamoto et al. ........... 424/65 |
| 5,753,251 A | 5/1998 | Burrell et al. .............. 424/426 |
| 5,766,240 A | 6/1998 | Johnson ......................... 623/2 |
| 5,770,255 A | 6/1998 | Burrell et al. ............... 427/2.1 |
| 5,798,115 A * | 8/1998 | Santerre et al. ............. 424/423 |
| 5,895,419 A * | 4/1999 | Tweden et al. ................ 623/2 |
| 5,895,420 A | 4/1999 | Mirsch, II et al. ............. 623/2 |
| 5,948,019 A * | 9/1999 | Shu et al. ...................... 623/2 |
| 6,015,816 A * | 1/2000 | Kostyniak et al. .......... 502/411 |
| 6,296,863 B1 * | 10/2001 | Trogolo et al. ............. 424/400 |
| 6,302,909 B1 * | 10/2001 | Ogle et al. ................ 427/2.24 |

* cited by examiner

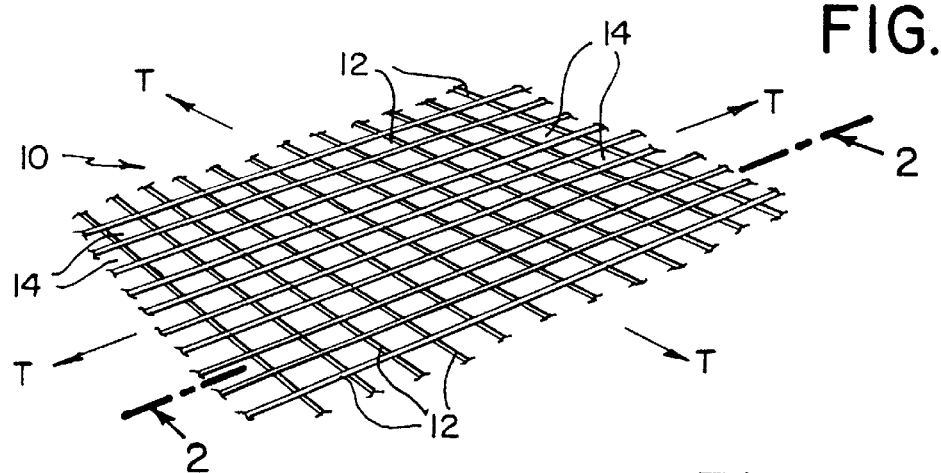
FIG. 1
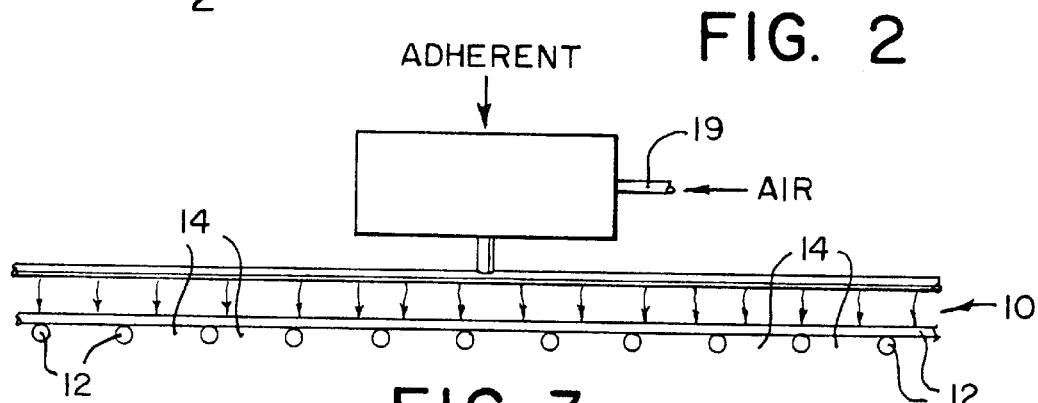
FIG. 2
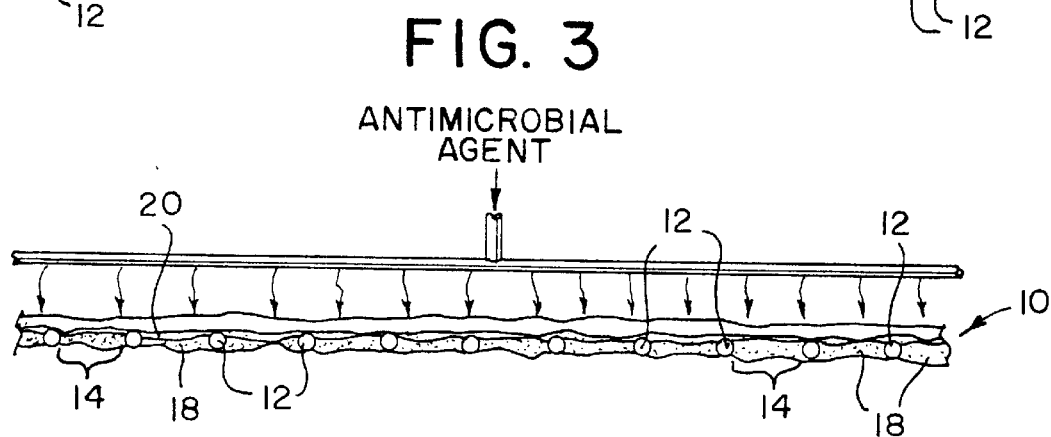
FIG. 3
FIG. 4

ANTIMICROBIAL SUTURING RING FOR HEART VALVE

Modern implantable prosthetic heart valves are typically formed of an annular valve seat in a relatively rigid valve body. One or more valve members, such as spheres, disks or leaflets, are movable between a closed, seated position in the annular valve seat and an open position over a prescribed range of motion. Such mechanical heart valves are typically formed of blood compatible, non-thrombogenic materials, typically currently comprising pyrolytic carbon and titanium. The rigid valve body is formed of a biocompatible material, such as a suitable metal or plastic. Valves made of human and porcine tissue also have been developed.

Some types of heart valves utilize a suturing ring surrounding the valve body. The ring is to be sewn by the surgeon to the peripheral tissue of a natural heart valve orifice (the "the valve rim") after surgical removal of damaged or diseased natural valve structure. The suturing ring is made of a fabric or other similar material which can be penetrated by the needle used by the surgeon to fasten the valve body to the heart tissue. In some cases, the suturing ring includes a part to which the fabric is fastened so that the ring can be rotated relative to the heart valve body. Such an arrangement is shown in U.S. Pat. No. 5,766,240.

BRIEF DESCRIPTION OF THE INVENTION

The present invention relates to a suturing ring for a heart valve body containing an inorganic antimicrobial agent. In a preferred embodiment the ring is of fabric material. The antimicrobial properties of such a suturing ring has advantages in that it is able to kill certain types of bacteria which are present in the body and which, at least in the initial stages of implantation of the heart valve, can have adverse effects relative to infection and rejection of the valve and also its proper operation. The antimicrobial fabric of the suturing ring of the invention is biocompatible, and presents no problem relative to its suturing by the surgeon. In a preferred embodiment of the invention, the antimicrobial agent is a zeolite.

The antimicrobial fabric for the suturing ring can be of a porous flexible material to accommodate heart movement or of a fabric that is fully coated with the antimicrobial agent. In either case, the fabric can be coated with a tissue compatible substance such as collagen.

The invention also provides a novel suturing ring having fabric material with an inorganic antimicrobial with the ring being rotatable relative to the heart valve body to permit its positioning relative to the heart tissue orifice.

OBJECTS OF THE INVENTION

It is therefore an object of the invention to provide a heart valve suturing ring including a fabric containing an inorganic antimicrobial agent.

Another object is to provide a suturing ring for a heart valve of porous fabric containing an inorganic antimicrobial agent.

An additional object is to provide a fabric suturing ring for a heart valve containing an inorganic antimicrobial agent which is coated by a tissue compatible substance.

Still a further object is provide a suturing ring for a heart valve having a fabric containing an inorganic antimicrobial agent which is rotatable relative to the heart valve body.

BRIEF DESCRIPTION OF THE DRAWINGS

Other objects and advantages of the present invention will become more apparent upon reference to the following specification and annexed drawings in which:

FIG. 1 is a perspective view of a base fabric;

FIG. 2 is a cross-sectional view along lines 2—2 of FIG. 1 showing application of the coating material to the fabric;

FIG. 3 is a cross-sectional view of the fabric after the antimicrobial agent has been applied;

FIG. 4 is a cross-sectional view of the finished fabric after drying;

DETAILED DESCRIPTION OF THE INVENTION

Figure 5:
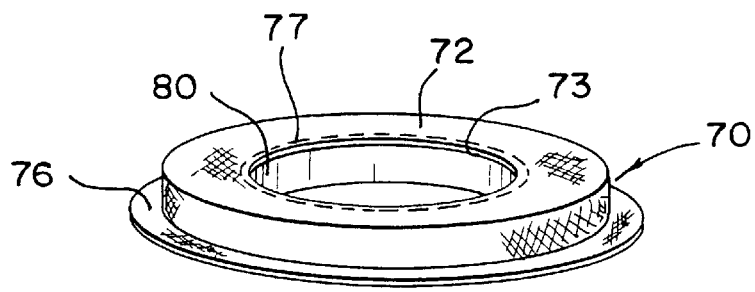
FIG. 5 is a perspective view of a heart valve fabric suturing ring according to the invention and FIG. 5A is a cross-section thereof.
Figure 5A:
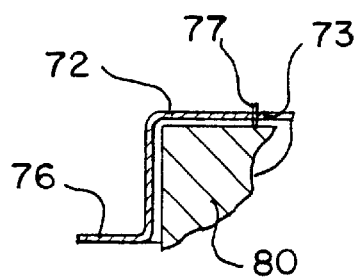

All patents, patent applications, and publications listed herein are hereby incorporated by reference in their entireties.

Various types of fabrics containing the antimicrobial agent suitable for use as the suturing ring are first described.

1. Porous fabric—FIGS. 1–4 show an embodiment of the invention for processing a fabric that is porous and flexible to be used for the suturing ring. Referring to FIG. 1, there is shown a base material comprising a piece of fabric 10 of the mesh type formed by fibers 12 which are laid transverse to each other and which define spaces, or pores, 14 between the fibers. The fibers can be of any suitable material, for example, cotton, nylon polyester, TEFLON® polytetrafluoroethylene (PTFE), e-PTFE and blends of these materials. For the suturing ring application, TEFLON® PTFE or polyester is preferred. The fabric can be either of the woven or non-woven type. The fabric 10 is shown by the arrows T as being able to be held under tension in both directions generally along the fabric length and width by any suitable mechanism (not shown), for example, rollers, clamps, etc.

FIG. 2 shows the fabric piece 10 in the stage of having a coating of an adherent material applied to one surface. It should be understood that the invention is applicable to performing the process on both fabric surfaces and on the sides which form the pores 14. The adherent coating material is a biologically compatible material such as, for example, acrylic, polyurethane, silicone, latex, polyglycolic lactic acid or other biodegradable polymer, especially one that is a hydrophilic, non-degrading polymer such as a hydrophilic polyurethane, for example TECOPHILIC which is made by Thermedics. These materials all have elastomeric properties.

In a preferred embodiment of the invention, the fabric coating material is applied as a mixture of a high strength RTV silicone material dispersed in a solvent, such as xylene. A preferred composition of the mixture is 50% RTV silicone and 50% xylene although the ratio of the two silicone materials can be varied. Increasing the proportion of the coating material in the mixture make the final product less pliable.

In a preferred manner of application of the coating material, the fabric 10 is held under tension in its lengthwise dimension. The coating material-solvent mixture is supplied by a peristaltic pump to an ultrasonic disperser. The ultrasonic disperser creates a fine mist of the mixture that is blown out of the disperser by an air source, illustratively shown by reference numeral 19, to coat the fabric 10. There can be one or more dispersers and air sources on both sides of the fabric and at varying angles to fully coat the entire surface of the fabric fibers. Alternatively, only one surface is coated, the two surfaces are coated sequentially, or both surfaces coated at the same time. In the application for the suturing ring the fabric is coated on both surfaces.

FIG. 3 shows the fabric 10 having been coated on one side with the coating material mixture. As seen, the coating material 18 extends into the openings 14 between the fibers of the fabric and also coats the top of each of the fibers. There is a continuous layer of the coating material 18 over the fabric at this stage of the process, that is, the coating material fills the pores 14. The fabric can be cycled relative to the disperser as many times as needed. That is, the deposition of the coating material mixture on the fabric can be accomplished by applying a desired number of layers to achieve a desired thickness. The layers are contiguous to and mixed with each other. The depth of the coating material 18 on top of the fabric is selected to be between 0.01 and 50 microns, more preferably between 0.1 and 25 microns, and most preferably between 0.1 and 10 microns.

As is also shown in FIG. 3, an inorganic antimicrobial agent 20 in powdered form is applied to the coating material 18 while it is still wet. During this step the fabric preferably is held under tension in both directions, that is, generally along both the fabric fibers' cross-direction. The powdered antimicrobial agent 20 becomes immersed into and bonds with the coating material layer 18 on the fabric. The xylene evaporates from the coating.

As to the inorganic antimicrobial agent 20, a number of metal ions, which are inorganic materials, have been shown to possess antibiotic activity, including silver, copper, zinc, mercury, tin, lead, bismuth, cadmium, chromium and thallium ions. These antibiotic metal ions are believed to exert their effects by disrupting respiration and electron transport systems upon absorption into bacterial or fungal cells. Antimicrobial metal ions of silver, gold, copper and zinc, in particular, are considered safe even for in vivo use. Antimicrobial silver ions are particularly useful for in vivo use due to the fact that they are not substantially absorbed into the body. That is, if such materials are used for the antimicrobial fabric, they should pose no hazard to the body.

Antibiotic zeolites also are suitable as the agent. These have been prepared by replacing all or part of the ion-exchangeable ions in zeolite with ammonium ions and antibiotic metal ions, as described in U.S. Pat. Nos. 4,938,958 and 4,911,898. Such zeolites have been incorporated in antibiotic resins (as shown in U.S. Pat. Nos. 4,938,955 and 4,906,464) and polymer articles (U.S. Pat. No. 4,775,585). Polymers including the antibiotic zeolites have been used to make refrigerators, dish washers, rice cookers, plastic film, chopping boards, vacuum bottles, plastic pails, and garbage containers. Other materials in which antibiotic zeolites have been incorporated include flooring, wall paper, cloth, paint, napkins, plastic automobile parts, catheters, bicycles, pens, toys, sand, and concrete. Examples of such uses are described in U.S. Pat. Nos. 5,714,445; 5,697,203; 5,562,872; 5,180,585; 5,714,430; and 5,102,401. These applications involve slow release of antibiotic silver from the zeolite particles which is suitable for the antimicrobial fabric.

Antibiotic zeolites are well-known and can be prepared for use in the present invention using known methods. These include the antibiotic zeolites disclosed, for example, in U.S. Pat. Nos. 4,938,958 and 4,911,898.

In a preferred embodiment of the invention, the inorganic antibiotic metal containing composition is an antibiotic metal salt. Such salts include silver iodate, silver iodide, silver nitrate, and silver oxide. Silver nitrate is preferred. These salts are particularly quick acting, as no release from ceramic particles is necessary to function antimicrobially.

Antibiotic ceramic particles useful with the present invention include zeolites, hydroxyapatite, zirconium phosphates or other ion-exchange ceramics. Hydroxyapatite particles containing antimicrobial metals are described, e.g., in U.S. Pat. No. 5,009,898. Zirconium phosphates containing antimicrobial metals are described, e.g., in U.S. Pat. Nos. 5,296,238; 5,441,717; and 5,405,644.

Either natural zeolites or synthetic zeolites can be used to make the antibiotic zeolites used in the present invention. "Zeolite" is an aluminosilicate having a three dimensional skeletal structure that is represented by the formula: $XM_2/nO-Al_2O_3-YSiO_2-ZH_2O$. M represents an ion-exchangeable ion, generally a monovalent or divalent metal ion, n represents the atomic valency of the (metal) ion, X and Y represent coefficients of metal oxide and silica respectively, and Z represents the number of water of crystallization. Examples of such zeolites include A-type zeolites, X-type zeolites, Y-type zeolites, T-type zeolites, high-silica zeolites, sodalite, mordenite, analcite, clinoptilolite, chabazite and erionite. The present invention is not restricted to use of these specific zeolites.

The ion-exchange capacities of these zeolites are as follows: A-type zeolite=7 meq/g; X-type zeolite=6.4 meq/g; Y-type zeolite=5 meq/g; T-type zeolite=3.4 meq/g; sodalite=11.5 meq/g; mordenite=2.6 meq/g; analcite=5 meq/g; clinoptilolite=2.6 meq/g; chabazite=5 meq/g; and erionite=3.8 meq/g. These ion-exchange capacities are sufficient for the zeolites to undergo ion-exchange with ammonium and antibiotic metal ions.

The specific surface area of preferred zeolite particles is preferably at least 150 $m^2$/g (anhydrous zeolite as standard) and the $SiO_2/Al_2O_3$ mol ratio in the zeolite composition is preferably less than 14, more preferably less than 11.

The antibiotic metal ions used in the antibiotic zeolites should be retained on the zeolite particles through an ion-exchange reaction. Antibiotic metal ions which are adsorbed or attached without an ion-exchange reaction exhibit a decreased bactericidal effect and their antibiotic effect is not long-lasting. Nevertheless, it is advantageous for imparting quick antimicrobial action to maintain a sufficient amount of surface adsorbed metal ion.

In the ion-exchange process, the antibiotic metal ions tend to be converted into their oxides, hydroxides, basic salts etc. either in the micro pores or on the surfaces of the zeolite and also tend to deposit there, particularly when the concentration of metal ions in the vicinity of the zeolite surface is high. Such deposition tends to adversely affect the bactericidal properties of ion-exchanged zeolite.

In an embodiment of the antibiotic zeolites, a relatively low degree of ion exchange is employed to obtain superior bactericidal properties. It is believed to be required that at least a portion of the zeolite particles retain metal ions having bactericidal properties at ion-exchangeable sites of the zeolite in an amount less than the ion-exchange saturation capacity of the zeolite. In one embodiment, the zeolite employed in the present invention retains antimicrobial metal ions in an amount up to 41% of the theoretical ion-exchange capacity of the zeolite. Such ion-exchanged zeolite with a relatively low degree of ion-exchange may be prepared by performing ion-exchange using a metal ion solution having a low concentration as compared with solutions conventionally used for ion exchange.

The antibiotic metal ion is preferably present in the range of from about 0.1 to 20 wt. % of the zeolite. In one embodiment, the zeolite contain from 0.1 to 20 wt. % of silver ions and from 0.1 to 20 wt. % of copper or zinc ions. Although ammonium ion can be contained in the zeolite at a concentration of about 20 wt. % or less of the zeolite, it is desirable to limit the content of ammonium ions to from 0.5 to 15 wt. %, preferably 1.5 to 5 wt. %. Weight % described herein is determined for materials dried at temperatures such as 110° C., 250° C. or 550° C. as this is the temperature employed for the preferred post-manufacturing drying process.

A preferred antibiotic zeolite is type A zeolite containing either a combination of ion-exchanged silver, zinc, and ammonium or silver and ammonium. One such zeolite is manufactured by Shinegawa, Inc. under the product number AW-10N and consists of 0.6% by weight of silver ion-exchanged in Type A zeolite particles having a diameter of about 2.5μ. Another formulation, AJ-10N, consists of about 2% by weight silver ion-exchanged in Type A zeolite particles having a diameter of about 2.5μ. Another formulation, AW-80, contains 0.6% by weight of silver ion-exchanged in Type A zeolite particles having a diameter of about 1.0μ. Another formulation, AJ-80N, consists of about 2% by weight silver ion-exchanged in Type A zeolite particles having a diameter of about 1.0μ. These zeolites preferably contain about between 0.5% and 2.5% by weight of ion-exchanged ammonium.

In a preferred embodiment, the agent can be of the type designated HealthShield, which is sold by the assignee of the subject application. This material is basically a zeolite, this being a metal having one or the whole of the metal substituted by at least one kind of an ion exchangeable metal selected from the group consisting of Ag, Cu and Zn.

In accordance with the invention, other inorganic antimicrobial agents, i.e., those containing silver, copper, lead, gold tin, zinc and mercury. can be used.

A typical particle size for the antimicrobial agent is between 0.8 and 10 microns and the agent is dispersed on the coating material 18 in the quantity of between 0.5 and 25% by weight, more preferably between 0.5 and 10% and most preferably between 1.5 and 5% of the matter that remains on the fabric, exclusive of the fabric. The particles adhere to the coating material while it is wet and become embedded in the coating material 18 as it dries.

As shown in FIG. 4, after the antimicrobial agent 20 is applied to the coating material 18, the product is cured, that is, dried, with air under pressure, for example at 60 psi. This removes all of the matter, coating material and antimicrobial agent, in the fabric pores 14. As shown, each of the fabric fibers has on one surface thereof the coating material 18 on top of which are the embedded particles of the antimicrobial agent 20. If both surfaces of the fabric are treated, the entirety of the fabric would have the same appearance. In any case, the fabric pores 14 would be clear. This maintains fabric pliability.

In another embodiment of making the antimicrobial fabric, the inorganic antimicrobial agent is blended into the textile coating material mixture, such as of the type described above. The mixture is then applied to the base fabric by a spraying process, as previously described, or by dipping. Here also, the fabric is preferably held under tension. In each type of application of the mixture, the wet material is subjected to a blowing operation to remove matter from the pores so that it will retain its porosity. The coating materials can include, for example, acrylic, polyurethane, silicone, latex, polyglycolic lactic acid or other biodegradable polymer, especially one that is a hydrophilic, a non-degrading polymer such as a hydrophilic polyurethane, for example TECOPHILIC which is made by Thermedics. Use of antimicrobial agents in hydrophilic materials is also described in an application filed on even date herewith, assigned Ser. No. 09/197,815 and entitled "Antibiotic Hydrophilic Polymer Coating". The inorganic antimicrobial agent mixed with the coating material is one of the type discussed above and the concentration of the agent in the dry coating material is 0.01 to 50%, preferably 0.1 to 20% and most preferably from 0.5 to 10%.

The resulting fabric, made either by applying the inorganic agent to an adherent coating material or as part of a mixture with the coating material, is a piece of fabric that is antimicrobial, pliable and porous. The product can be used in medical applications and has antimicrobial properties.

An example of an embodiment of the porous fabric of the invention utilized the following:

| | |
|---|---|
| fiber material: | polyester |
| silicone mixture: | 50% RTV and 50% xylene |
| thickness of silicone layer: | 1–5 microns |
| agent particle size: | 1–2.5 microns |
| agent dispersal factor: | 1% |
| air pressure: | 60 psi |

Non-Porous Fabric—Using the process of FIGS. 1–4 and the described components and their variants, by eliminating the drying step by air under pressure and permitting drying of the fabric in a manner which does not remove the matter from the pores, the fabric will be fully coated with the inorganic agent. That is, the antimicrobial agent will be embedded in the coating material of the fabric fibers as well as in the fabric pores. Here, it is not absolutely necessary to hold the fabric under tension when the agent is applied to the fabric and the drying takes place. While the resulting fabric will not be as flexible, it still is satisfactory for use as a suturing ring.

Another way of making the non-porous antimicrobial fabric, other than by spraying the inorganic onto the fabric or dipping the fabric into the inorganic, is to provide a slurry of the inorganic and kneading it into the base fabric. A process of this type is described in U.S. Pat. 5,100,671. Here also the antimicrobial agent will remain in the fabric pores.

Fabric With Integral Antimicrobial Agent

In this type of fabric, the fibers are either of a plurality of the mono-filament type, such as of a plurality of polyester filaments, formed in bundles, such as by twisting, or of a naturally multi-filament type, such as cotton. The object is that the fibers themselves have spaces, gaps or voids into which the antimicrobial agent can be placed. For example, a dough or slurry of the antimicrobial agent is kneaded into a fabric of this type and the agent will be embedded in the spaces of the bundle of the plurality of mono-filaments forming a fiber or the fiber of natural material. The fabric can be made porous by holding it under tension and blowing out the agent from the pores, as described above. It can be left non-porous by permitting the agent to dry without attempting to remove the particles from the pores.

Antimicrobial Fabric Coated With Tissue Compatible Material

The porous fabric described above with respect to FIGS. 1–4, or the non-porous fabric, can be coated with a tissue growth promoting substance, for example, collagen. The collagen can be coated onto the fabric either before or after the fabric is shaped into the suturing ring. The collagen can be coated on one or both sides of the fabric and can be applied by spraying, dipping, painting, layering or any other suitable process. It is applied at least to the surface that is to be remote from the valve body, that is, exposed to the body tissue. The collagen material still permits the inorganic antimicrobial agent of the fabric to perform its function since it is effectively porous, being a skin type material.

FIG. 5 is a perspective view of a preferred embodiment of suturing ring 70 using the fabric containing an inorganic antimicrobial agent of the porous or non-porous types, whether coated with collagen or un-coated, as described above. The ring 70 has a top portion shoulder 72 of generally annular shape and a central opening 73. A step wall 74 depends downwardly from the annular shoulder 72 and at the bottom end of the step wall is an outwardly extending is an circumferential flange 76. The valve body, illustratively shown by 80 and illustratively shown as being of disc shape, fits within the ring between the shoulder 72 and the flange 76. The height of the step wall 74 generally corresponds to the height of the valve body 80. The opening 73 at the top of the ring can be reinforced, such as by stitching 77, so that the valve body can be firmly engaged.

To attach the heart valve body 80 to the heart, the body is placed within the ring 70 and oriented with the ring flange 76 positioned opposite the heart tissue. The surgeon then makes sutures through the flange 76 to the heart tissue. The valve body 80 will be firmly held relative to the heart between the flange 76 and the shoulder 72 with its reinforcement 77.

Once the valve body is attached, the inorganic antimicrobial agent of the suturing ring 70 fabric functions to kill bacteria from body parts and fluid that contact it. Thus, the suturing ring provides an added degree of protection against infection.

When the ring 70 is made of the porous fabric there is an advantage in that the porosity of the fabric allows fluid access to the valve body which maintains better temperature stability between the valve body and the heart.

Whether the fabric is porous or non-porous, it is preferred that the fabric forming the ring have the antimicrobial agent on both surfaces so that it also will be more active against bacteria and organisms between the ring and the heart valve body.

The ring 70 can be formed from the fabric by any suitable technique, such as cutting a piece of the fabric to size, making the opening 73, etc. Since the fabric 70 has the coating material 18, which can have shape retaining characteristics, some types of the fabric can be shaped by pressure or heat, or combination of the two, depending on the type of coating material. For example, if the fabric coating material 18 to which the agent is applied is an acrylic or other material with thermosetting properties, a slightly heated die can be used having the shape of ring 70. The heating is carried out at a level such as not to remove the coating material. If the fabric is to be heated to shape it into the ring, it is preferred that the collagen be applied after the heating.

The suturing ring 70 shown in FIG. 5 is only illustrative of the various types of rings that can be produced using the fabric of the invention which, as explained above, has the necessary antimicrobial properties as well as being able to be easily formed in the shape shown as well as to permit its attachment to tissue by sutures. In all cases, the antimicrobial action of the fabric reduces the possibility of infection occurring at the valve implantation site.

In some cases a suturing ring is used with a heart valve body that is non-circular or in which it is desired to be able to position the suturing ring relative to the body. Various arrangements for doing this are shown in U.S. Pat. No. 5,766,240. One of the embodiments of that patent is shown in FIGS. 6 and 6A adapted for using the novel inorganic antimicrobial fabric of the invention.

Figure 6:
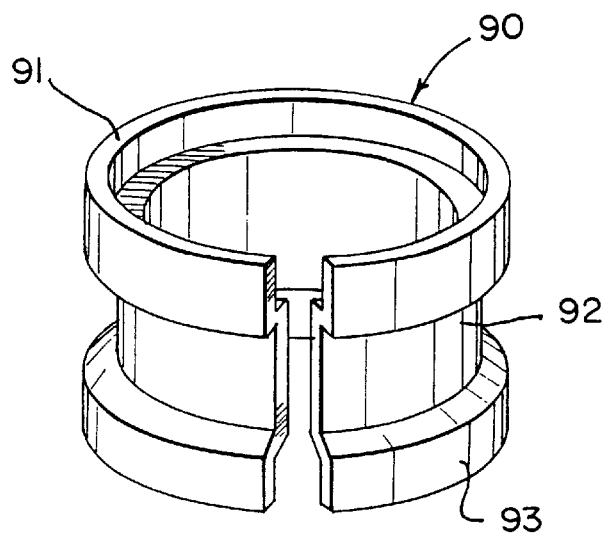
FIG. 6 is perspective view of a rotatable collar for a suturing ring.
Figure 6A:
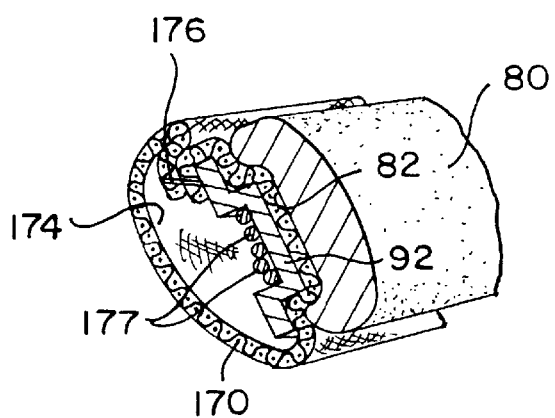
FIG. 6A is a cross sectional view showing the fabric of the invention applied.

Referring to FIGS. 6 and 6A, there is an annular collar 90 having upper and lower sections 91 and 93 between which is a depressed center section 92 which extends inwardly of sections 91 and 93. The collar center section 92 is to fit into a corresponding peripheral depression 82 in the outer wall of the valve body 80. Here the suturing ring 170 is formed by taking a piece of the fabric 170, laying it between the valve body groove 82 and the collar center section 92 which is press fit in the valve body groove 82. The fabric is played out to form a loose loop 174 of the fabric and the fabric ends are sewn at 176 to complete the ring. There are wraps of a cord 177 around the collar center section to prevent it from being damaged by a needle inadvertently making contact.

In using the arrangement of FIGS. 6 and 6A, the collar 90 holds the fabric suturing ring 170 in position relative to the valve body and is rotatable about the valve body to position the ring 170, as desired. The surgeon can manipulate the loose hanging ring loop 174, such as by pulling part of it down, so that sutures can be made through the ring 170 to the heart tissue. The use of the antimicrobial fabric is particularly advantageous in this type of a suturing ring since body fluid can be present in the space between the collar and the inner part of the ring which could create infection problems. The antimicrobial action of the fabric acts to prevent this.

The antibiotic properties of the antibiotic zeolite particles of the invention may be assayed while in aqueous formulations using conventional assay techniques, including for example determining the minimum growth inhibitory concentration (MIC) with respect to a variety of bacteria, eumycetes and yeast. In such a test, the bacteria listed below may be employed:

*Bacillus cereus* var *mycoides,*

*Escherichia coli,*

*Pseudomonas aeruginosa,*

*Staphylococcus aureus,*

*Streptococcus faecalis,*

*Aspergillus niger,*

*Aureobasiduim pullulans,*

*Chaetomium globosum,*

*Gliocladium virens,*

*Penicillum funiculosum,*

*Candida albicans,*

*Saccharomyces cerevisiae,*

The assay for determining MIC can be carried out by smearing a solution containing bacteria for inoculation onto a plate culture medium to which a test sample of the encapsulated antibiotic zeolite particles is added in a particular concentration, followed by incubation and culturing of the plate. The MIC is defined as a minimum concentration thereof required for inhibiting the growth of each bacteria.

The present invention will hereunder be explained in more detail with reference to the following non-limiting working examples.

EXAMPLE 1

A 1"×1" sample of knitted polyester, available from Bard Vascular Systems Division as knitted polyester style no. 6103, was coated with an antibiotic hydrophilic coating as follows.

A coating solution containing 2.90% by weight of hydrophilic polyurethane available as Tecophilic™ from Thermedics; 96.81% tetrahydrofuran; and 0.29% AW-10N zeolite, available from Shinagawa, Inc., was prepared and mixed with a high shear mixer.

An eye dropper was used to apply the coating solution to the polyester sample. The polyester sample was then sprayed with air to remove excess powder and cure the coating.

EXAMPLE 2

A Dow Shaker Test was performed on the polyester sample prepared in Example 1 (hereafter referred to as Sample A) to determine its inhibitory effect against *S. aureus*. The Dow Shaker Test is based on Dow Corporate Test Method 0923 for testing aerobic bacteria by Dow Chemical. The Dow Shaker Test is described below.

Sample A was sterilized at 121° C. for 15 minutes.

A culture tube containing *S. aureus* was prepared by adding one disk of *S. aureus* to the culture tube. From about 2 to 5 ml of broth was added to the culture tube. Then the culture tube was agitated with a vortex mixer until the disk was completely dissolved in the broth. The bacteria in the culture tube was incubated for at least 3 hours at 35° C. The culture tube was then refrigerated at about 2–8° C. until needed for testing.

A 5 ml sample of bacteria from the culture tube was removed and agitated in a vortex mixer. The absorbance of the sample was measured at 475 nm with a spectrophotometer relative to the absorbance of the aforementioned broth. Broth and/or bacteria from the culture tube were added to the sample until an absorbance of about 0.1 absorbance units was obtained. This corresponded to from about $10^5$ to about $10^6$ colony forming units per milliliter (CFU/ml).

5 ml of suspension was extracted from the sample and added to a flask containing 70 ml of sterile buffer. The resulting solution contained from about $10^4$ to about $10^5$ CFU/ml. The flask was capped and shaken on a wrist action shaker for 1 minute at maximum speed. This is referred to as time "0 hours" below.

The number of colony forming units in 1 ml of the solution was determined at time 0 hours by the following procedure. 1 ml of solution was extracted from the flask and added to a vial containing 9 ml of buffer solution to form a 10:1 dilution. The solution was repeatedly diluted with buffer solution until a plate count of about 30 to about 200 CFU/ml was obtained.

1 ml of the solution from the flask and each dilution were transferred to separate petri dishes. About 15–20 ml of molten agar was added to each dish. Each dish was rotated 10 times clockwise and 10 times counter-clockwise to evenly distribute the agar and bacteria. Then, each dish was incubated for 18–24 hours at 35° C. A plate count was performed on the petri dish containing from about 30 to about 200 bacteria colony forming units to determine the number of colony forming units.

Also, at time 0 hours, sample A was added to the flask and shaken with a wrist action shaker for 1 hour. The number of colony forming units in 1 ml of the solution in the flask was determined by the procedure above using 2 petri dishes. If the numbers of colony forming units in the 2 petri dishes were not within 15% of each other, the entire Dow Shaker Test was repeated.

The number of colony forming units in 1 ml of the solution was also determined after shaking the flask with a wrist action shaker for 18 and 24 hours.

A control was tested by the same procedure as sample A. The control was a 1"×1" sample of knitted polyester, available from Bard Vascular Systems Division as knitted polyester style no. 6103.

The number of colony forming units at times 0 hours, 1 hour, 18 hours, and 24 hours for sample A and the control are in Table 1. The percentage of bacteria killed by sample A and the control at times 1 hour, 18 hours, and 24 hours are in Table 2.

TABLE 1

| Sample | Bacteria Counts of *S. aureus* (Colony Forming Units) | | | |
| --- | --- | --- | --- | --- |
| | 0 hours | 1 hour | 18 hours | 24 hours |
| Sample A | 780,000 | 2,145,000 | 85,000 | 3,700 |
| Control | 480,000 | 12,400,00 | 4,720,00 | 4,300,000 |

TABLE 2

| Sample | % Killed | | |
| --- | --- | --- | --- |
| | 1 hour | 18 hours | 24 hours |
| Sample A | 0 | 89.10% | 99.53% |
| Control | 0 | 0 | 0 |

As indicated in Table 2, Sample A exhibited 99.53% inhibition of *S. aureus* after 24 hours of contact with the bacteria.

EXAMPLE 3

Safety and biocompatibility tests were conducted on the antibiotic zeolites employed in the invention. ISO 10993-1 procedures were employed. The following results were obtained:

| | |
| --- | --- |
| Cytotoxicity: | Non-Toxic |
| Acute Systemic Toxicity: | Non-Toxic |
| Intracutaneous Toxicity: | Passed |
| Skin Irritation Test: | Non-Irritant |
| Chronic Toxicity: | No Observable Effect |
| In-vitro Hemolysis: | Non-Hemolytic |
| 30-day Muscle Implant Test: | Passed |
| 60-day Muscle Implant Test: | Passed |
| 90-day Muscle Implant Test: | Passed |
| Ames Mutagenicity Test: | Passed |
| Pyrogenicity: | Non-Pyrogenic |

Thus, the antibiotic zeolites are exceptionally suitable under relevant toxicity and biocompatibility standards for use in the fabric.

We claim:

1. An implantable heart valve having at least one heart valve mechanism and a suturing ring for suture attachment of the valve to heart tissue, wherein the suturing ring comprises a fabric and a coating material on said fabric, said coating material comprising a) a material selected from the group consisting of acrylic, polyurethane, silicone, latex, polyglycolic lactic acid, a biodegradable polymer, a hydrophilic biodegradable polymer, and a non-degrading polymer and b) an inorganic antimicrobial agent comprising a zeolite having ion-exchanged antimicrobial metal ions said zeolite being present at a surface of the suture ring such that inorganic antimicrobial metal ion are antimicrobially available.

2. An implantable heart valve as in claim 1 wherein said fabric is porous.

3. An implantable heart valve as in claim 1 wherein said fabric is coated with collagen.

4. An implantable heart valve as in claim 1 wherein said heart valve has a valve body with top and bottom surfaces and a valve body wall therebetween, said suturing ring having an annular top part fitting over one of said top and bottom surfaces and defining an opening to said heart valve and a step wall depending from said annular top part to extend along said valve body wall.

5. An implantable heart valve as in claim 4 wherein said suturing ring further comprises a flange ring extending outwardly from the end of said step wall opposite said annular top part.

6. An implantable heart valve as in claim 1 wherein said non-degrading polymer is a hydrophilic polyurethane.

7. An implantable heart valve as in claim 1 wherein the fibers of said fabric are selected from the group consisting of cotton, nylon, polyester, polytetrafluroethylene, e-polytetrafluoroethylene, and blends of these materials.

8. An implantable heart valve as in claim 1 wherein said antimicrobial metal ions are selected from the group consisting of silver, zinc, copper and combinations of silver and copper or silver and zinc ions.

9. An implantable heart valve as in claim 1 wherein said inorganic antimicrobial agent is present in the coating material in the quantity of between 0.5 and 25% by weight based on dry weight of the coating material.

10. An implantable heart valve as in claim 9 wherein the antimicrobial agent is in particulate form and the particle size of the agent is between 0.8 and 10 microns.

11. An implantable heart valve as in claim 1 wherein the fiber of said fabric is polyester and said coating material is a hydrophilic polymer.

12. An implantable heart valve as in claim 1 wherein the antimicrobial agent is applied to the coated fabric while the coating is still wet.

13. An implantable heart valve having at least one heart valve mechanism, and a suturing ring for suture attachment of the valve to heart tissue, wherein the suturing ring comprises a fabric, the fibers of which are coated with an elastomeric coating material containing an inorganic antimicrobial agent comprising an inorganic antimicrobial metal ion component, said antimicrobial agent being present at a surface of the suture ring such that inorganic antimicrobial metal ion is antimicrobially available.

14. The implantable heart valve of claim 13 wherein the antimicrobial agent is in the form of antibiotic ceramic particles.

15. The implantable heart valve of claim 14 wherein the antibiotic ceramic particles comprise an ion-exchange type antimicrobial agent selected from the group consisting of antimicrobial zeolites, hydroxy apatites, zirconium phosphates and other ion-exchange type ceramics.

16. The implantable heart valve of claim 14 wherein the antimicrobial metal ion is selected from the group consisting of silver, copper, zinc, gold, and combinations of silver and copper or silver and zinc.

17. An implantable heart valve as in claim 14 wherein said coating material is selected from the group consisting of acrylic, polyurethane, silicone, latex, polyglycolic lactic acid, a biodegradable polymer, a hydrophilic biodegradable polymer, and a non-degrading polymer.

18. An implantable heart valve as in claim 14 wherein the fibers of said fabric are selected from the group consisting of cotton, nylon, polyester, polytetrafluoroethylene, e-polytetrafluoroethylene and blends of these materials.

19. An implantable heart valve as in claim 14 wherein the antimicrobial agent is applied to the coated fabric while the coating is still wet.

20. An implantable heart valve as in claim 14 wherein said inorganic antimicrobial agent is present in the coating material in the quantity of between 0.5 and 25% by weight based on dry weight of the coating material.

21. An implantable heart valve as in claim 13 wherein the fiber of said fabric is polyester, said coating material is a hydrophilic polymer and said antimicrobial agent is an antimicrobial zeolite.

22. An implantable heart valve as in claim 13 wherein the antimicrobial agent is an antimicrobial zirconium phosphate.

23. An implantable heart valve as in claim 1 wherein the antimicrobial agent is dispersed throughout the coating material.

24. An implantable heart valve as in claim 14 wherein the antimicrobial agent is dispersed throughout the coating material.

* * * * *